United States Patent
Schnatterer et al.

(10) Patent No.: US 9,464,038 B2
(45) Date of Patent: Oct. 11, 2016

(54) METHOD FOR PRODUCING SPECIFIC OXIMES AND OXIMETHERS

(71) Applicant: BAYER CROPSCIENCE AKTIENGESELLSCHAFT, Monheim am Rhein (DE)

(72) Inventors: Albert Schnatterer, Leverkusen (DE); Dieter Heinz, Leverkusen (DE); Martin Littmann, Leverkusen (DE); Ulrich Philipp, Odenthal (DE); Juergen Ludwig, Odenthal (DE); Constantin Frerick, Weil am Rhein (DE); Michael Barz, Moehlin (CH)

(73) Assignee: BAYER CROPSCIENCE AKTIENGESELLSCHAFT, Monheim Am Rhein (DE)

( * ) Notice: Subject to any disclaimer, the term of this patent is extended or adjusted under 35 U.S.C. 154(b) by 0 days.

(21) Appl. No.: 14/892,114

(22) PCT Filed: May 20, 2014

(86) PCT No.: PCT/EP2014/060278
§ 371 (c)(1),
(2) Date: Nov. 18, 2015

(87) PCT Pub. No.: WO2014/187791
PCT Pub. Date: Nov. 27, 2014

(65) Prior Publication Data
US 2016/0107986 A1    Apr. 21, 2016

(30) Foreign Application Priority Data
May 21, 2013 (EP) .................................. 13168466

(51) Int. Cl.
*C07C 249/08* (2006.01)
*C07F 9/09* (2006.01)

(52) U.S. Cl.
CPC ............... *C07C 249/08* (2013.01); *C07F 9/09* (2013.01)

(58) Field of Classification Search
CPC .................................. C07C 249/08; C07F 9/09
See application file for complete search history.

(56) References Cited

U.S. PATENT DOCUMENTS

| 3,443,887 | A | * | 5/1969 | Swanson | ................. C07C 45/48 423/592.1 |
| 5,488,161 | A | * | 1/1996 | Krbechek | ............. C07C 251/48 564/259 |
| 2008/0188460 | A1 | | 8/2008 | Casara et al. | |

FOREIGN PATENT DOCUMENTS

WO        9319041 A1    9/1993

OTHER PUBLICATIONS

International Search Report from PCT/EP2014/060278, mailed Aug. 7, 2014.
Chemistry and Industry, Feb. 22, 1969, pp. 240-241.
Porcheddu et al., "Synthesis of oximes and hydroxamic acids", Patai Series, Chapter 6, The chemistry of Hydroxylamines, Oximes and Hydroxamic Acids, Wiley 2009, pp. 163-231.
Mueller et al., "Methoden Der Organischen Chemie", Houben-Weyl, 1968, 43 pages.
Buechel et al., "Methoden Der Organischen Chemie", Houben-Weyl, 1990, 103 pages.
Osadchenko et al., "Phase-Transfer Catalysis in Synthesis of Oximes", State Research Institute of Organic Chemistry and Technology, Moscow, Russia, Russian Journal of Applied Chemistry, vol. 75, No. 3, 2002, pp. 511-512.

* cited by examiner

*Primary Examiner* — Golam M M Shameem
(74) *Attorney, Agent, or Firm* — McBee Moore Woodward Vanik, IP LLC

(57) ABSTRACT

Method for preparing certain oximes and oxime O-methyl ethers by reacting poorly water-soluble carbonyl compounds with salts of hydroxylamine or hydroxylamine O-methyl ether or the free base of hydroxylamine in the presence of certain phosphoric esters or salts thereof of the formula (I)

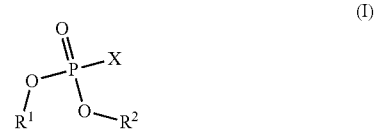

(I)

wherein $R^1$, $R^2$ and X are defined as specified in the description.

4 Claims, No Drawings

METHOD FOR PRODUCING SPECIFIC OXIMES AND OXIMETHERS

CROSS REFERENCE TO RELATED APPLICATIONS

This application is a §371 National Stage Application of PCT/EP2014/060278, filed 20 May 2014, which claims priority to EP 13168466.4, filed 21 May 2013.

BACKGROUND

1. Field of the Invention

The present invention relates to an improved method for preparing certain oximes and oxime O-methyl ethers by reacting poorly water-soluble carbonyl compounds with salts of hydroxylamine or hydroxylamine O-methyl ether or the free base of hydroxylamine in the presence of certain phosphoric esters or salts thereof.

2. Description of Related Art

Methods for preparing oximes and oxime O-methyl ethers are known (see e.g. Houben Weyl, Methoden der Organischen Chemie, Vol. E14b, pp. 287-384, 1990, Patai Series, The Chemistry of Hydroxylamines, Oximes and Hydroxamic Acids, pp. 163-231, Wiley 2009). A known representative of the oxime substance class is cyclohexanone oxime, which is a precursor for preparing polyamide. Oximes and oxime ethers play an important role as intermediates in the manufacture of active ingredients of e.g. plant protection agents and pharmaceuticals.

Oximes and oxime O-methyl ethers are often prepared by reacting carbonyl compounds with hydroxylamine or hydroxylamine O-methyl ether. The hydroxylamine—if used as the free base—is commercially available, usually as a 50% aqueous solution. The free base is very reactive, which makes the handling technically difficult. In the reaction, particularly on an industrial scale, salts of hydroxylamine and hydroxylamine O-methyl ether are more easily handled and are, in addition, considerably more cost-effective. Known salts are hydroxylammonium sulphate and chloride and hydroxylamine O-methyl ether hydrochloride. In the industrial reaction, it is always advantageous to use convenient starting materials which are also easy to handle since they may be used, for example, as a solid or an aqueous solution.

In the reaction of carbonyl compounds with salts of hydroxylamine or hydroxylamine O-methyl ether or the free base of hydroxylamine, very polar solvents must be used due to the polar properties of hydroxylamine and salts thereof. Solvents used include water, alcohols or alcohol/water mixtures, pyridine or DMSO (see Houben Weyl, Methoden der Organischen Chemie, Vol. X/4, 1968, pp. 55-91, Chem. Ind. 240, 1969). Despite using such solvents, the salts of the particularly inexpensive hydroxylammonium sulphate are frequently not sufficiently reactive under these conditions, particularly when carbonyl compounds with very low water solubility are involved, for which reason the hydroxylammonium chloride is usually employed in the synthesis. After the reaction using the polar solvents, moreover, a complex reaction mixture usually results which, in addition to the desired product, comprises an equivalent salt, the strongly polar solvent and optionally water. Such reaction mixtures are generally unsuitable for direct further processing. The workup of such a reaction mixture is complex and expensive however, especially for industrial production, since the polar solvent must be completely removed, by distillation for example, before the aqueous salt solution can be separated off and disposed of. A procedure in water without organic solvent, but with addition of long-chain perfluorinated carboxylic acids as phase transfer catalysts, is described in the Russian Journal of Applied Chemistry Vol 75, 511, 2002. A disadvantage of this process is the use of expensive perfluorinated compounds and the limitation to carbonyl compounds which are liquid under the reaction conditions.

The disadvantages of the prior art have now been overcome by an improved method, wherein the reaction takes place in a mixture of at least 2 liquid phases (at least a biphasic system), and in which the desired oxime or the desired oxime O-methyl ether can be prepared with high chemical yield and high conversion rates. Especially with the method, all poorly water-soluble carbonyl compounds (particularly aldehydes, ketones and quinones) can in principle be favourably reacted with a hydroxylamine salt or a salt of hydroxylamine O-methyl ether.

SUMMARY

The present invention provides a method for preparing oximes of the formula (Va) or oxime O-methyl ethers of the formula (Vb)

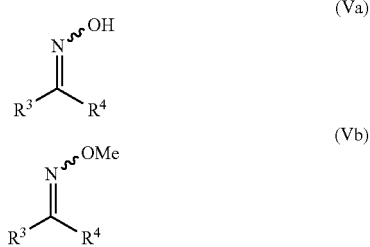

in which $R^3$ is $C_1$-$C_{12}$-alkyl, $C_3$-$C_{12}$-cycloalkyl, $C_2$-$C_{20}$-alkenyl, $C_6$-$C_{14}$-aryl, $C_1$-$C_6$-alkylaryl, 5-10-membered heterocycles and $C_1$-$C_6$-alkylhetaryl, wherein the alkyl residue, the cycloalkyl residue, the alkenyl residue, the aryl residue, the alkylaryl residue or the heterocyclic residue or the alkylhetaryl residue may be substituted with one or more substituents selected from among halogen, CN, $NO_2$, $C_1$-$C_6$-alkyl, $C_1$-$C_6$-haloalkyl, —OH, —OR, —COOR, =N—OR, $CONH_2$, CONHR, CONRR', SR, RSO, $RSO_2$, —OAr, carbonyl, =NOH;

$R^4$ is hydrogen, $C_1$-$C_{18}$-alkyl, $C_3$-$C_{12}$-cycloalkyl, $C_6$-$C_{14}$-aryl, $C_1$-$C_6$-alkylaryl, COOR, $CONH_2$, CONHR, CONRR', wherein the alkyl residue, the cycloalkyl residue, the aryl residue, the alkylaryl residue or the group R or R' may be substituted with one or more substituents selected from among halogen, CN, $NO_2$, $C_1$-$C_6$-alkyl, $C_1$-$C_6$-haloalkyl, OH, OR, COOR, C=N—OR, $CONH_2$, CONHR, CONRR', SR, RSO, $RSO_2$, OAr, carbonyl, =N—OH and R and R' are mutually independently unsubstituted or substituted $C_1$-$C_6$-alkyl; or $R^3$ and $R^4$ together form an unsubstituted or substituted cycloalkyl residue having 3 to 10 carbon atoms, preferably cyclopentyl, cyclohexyl, 4-methylcyclohexyl, cycloheptyl, cyclooctyl or mono- or bicyclic terpenes, or a substituted or unsubstituted 5-10-membered heterocycle;

comprising the reaction of a quinone, or a carbonyl compound of the formula (II)

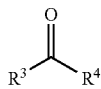
(II)

in which the residues $R^3$ and $R^4$ have the meanings mentioned above and the compounds (II) have a solubility in water of 0 to 30 g/l, preferably 0 to 20 g/l at 20° C., with the free base of hydroxylamine of the formula (III) or with a salt of hydroxylamine or hydroxylamine O-methyl ether of the formula (IV)

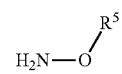
(III)

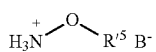
(IV)

in which
$R^5$ is hydrogen,
$R'^5$ is hydrogen or methyl,
$B^-$ if is an anion, which is selected from among chloride, sulphate, phosphate, hydrogen phosphate, dihydrogen phosphate, carbonate, hydrogen carbonate and acetate, and
in the presence of a phosphoric ester of the general formula (I) or a salt thereof,

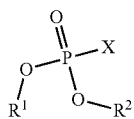
(I)

in which
X is OH and
$R^1$ and $R^2$ are mutually independently hydrogen, $C_1$-$C_{18}$-alkyl, $C_2$-$C_{20}$-alkenyl, $C_3$-$C_{12}$-cycloalkyl, phenyl or $C_1$-$C_6$-alkylphenyl, wherein the alkyl residue, the alkenyl residue or the cycloalkyl residue may be substituted in each case with one or more substituents selected from among halogen, CN and $NO_2$ and wherein the phenyl residue may in addition be mono- or polysubstituted with $C_1$-$C_6$-alkyl and/or $C_1$-$C_6$-haloalkyl;
in an at least biphasic mixture consisting of an aqueous and organic phase wherein the pH (at RT) in the aqueous phase during the reaction is in the range of 2 to 10.

DETAILED DESCRIPTION OF A PREFERRED EMBODIMENT

The reaction is effected at a pH in the range of 2 to 10, preferably in the range of 3 to 8, and wherein the reaction is optionally effected in the presence of a base and in an at least biphasic mixture, wherein the at least biphasic mixture consists of an aqueous phase and an organic phase and the organic phase is composed of a solvent or a solvent mixture which may be used in accordance with the invention. The organic phase may be formed by the reactant, i.e. the carbonyl compound.

The present invention also relates to the use of phosphoric esters of the general formula (I)

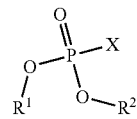
(I)

in which
X is OH and
$R^1$ and $R^2$ are mutually independently hydrogen, $C_1$-$C_{18}$-alkyl, $C_2$-$C_{20}$-alkenyl, $C_3$-$C_{12}$-cycloalkyl, phenyl or $C_1$-$C_6$-alkylphenyl, wherein the alkyl residue, the alkenyl residue or the cycloalkyl residue may be substituted in each case with one or more substituents selected from among halogen, CN and $NO_2$ and wherein the phenyl residue may in addition be mono- or polysubstituted with $C_1$-$C_6$-alkyl and/or $C_1$-$C_6$-haloalkyl;
for preparing oximes and oxime O-methyl ethers proceeding from quinones, or a carbonyl compound, which have a solubility in water of 0 to 30 g/l at 20° C., with a hydroxylamine salt or a hydroxylamine O-methyl ether salt, at a pH (RT) in the range of 2 to 10, optionally in the presence of a base, in an at least biphasic mixture, which consists of an aqueous phase and an organic phase.

Phosphoric esters of the general formula (I) are preferably used in the method according to the invention

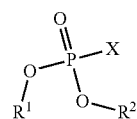
(I)

in which
X is OH; and
$R^1$ and $R^2$ are mutually independently hydrogen, $C_1$-$C_{18}$-alkyl, $C_2$-$C_{20}$-alkenyl, $C_3$-$C_{12}$-cycloalkyl, phenyl or $C_1$-$C_6$-alkylphenyl, wherein the alkyl residue, the alkenyl residue, or the cycloalkyl residue may be substituted in each case with one or more substituents selected from F, Cl, Br, I, CN, $NO_2$, and wherein phenyl may additionally be mono- or polysubstituted with methyl, ethyl, propyl or butyl and/or $CF_3$, $CH_2F$, $CHF_2$, $CH_2CF_3$ or $CH_2$—$CHF_2$, and also salts thereof, wherein the phosphoric ester may be a mono- or diester.

Particular preference is given to phosphoric esters of the general formula (I)

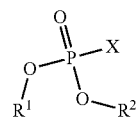
(I)

in which

X is OH; and $R^1$ and $R^2$ are mutually independently ethyl, butyl, hexyl, octyl, dodecyl or 9-octadecenyl.

The residues $R^1$ and $R^2$ are to be selected such that the phosphoric ester is sufficiently soluble in the solvent used or, if no solvent is present, in the relevant reactants.

Residues $R^1$ and $R^2$ are preferably ethyl, butyl, hexyl, octyl, dodecyl, and 9-octadecenyl.

Phosphoric esters of the formula (I) are especially preferably di(2-ethylhexyl)phosphoric acid, di-n-butylphosphoric acid, mono-n-butylphosphoric acid or monooleylphosphoric acid, while very particular preference is given to di(2-ethylhexyl)phosphoric acid.

In the present case, the use of the term "phosphoric ester" shall comprise mono- or diesters of phosphoric acid and the salts thereof.

Salt of phosphoric ester of the formula (I) where X=OH is understood to mean those salts in which the hydroxyl group is deprotonated and an alkali metal cation, alkaline earth metal cation or metals from the boron-aluminium group (so-called earth metals) is present as a counterion (e.g. $Li^+$, $Na^+$, $K^+$, $Mg^{2+}$, $Ca^{2+}$ and $Al^{3+}$). It is irrelevant for the invention whether the compound of the formula (I) where X=OH is used as a salt or in protonated form. Mixtures of different salts of phosphoric esters of the formula (I) may also be used.

The phosphoric ester of the formula (I) is used in accordance with the method of the invention in amounts in the range of 0.05 mol % or 0.01 mol % to 10 mol %, preferably in the range of 0.05 mol % or 0.01 mol % to 5 mol %, particularly preferably in the range 0.05 mol % or 0.01 mol % to 2 mol %, based on the carbonyl compound, in particular based on a carbonyl compound of the formula (II) or the quinone.

In the reaction of the poorly water-soluble carbonyl compound with the hydroxylamine salt or hydroxylamine O-methyl ether salt, the phosphoric ester serves as reaction mediator and cation scavenger. Diesters of phosphoric acids are known compounds and particular representatives are commonly used as extractants for metals (Journal of Inorganic and Nuclear Chemistry, 36, 189, 1974). Known representatives are di(2-ethylhexyl)phosphoric acid and di-n-butylphosphoric acid.

Aldehydes, ketones of the formula (II) and quinones may be used in the method according to the invention. Also included among the carbonyl compounds according to the invention are derivatives of these carbonyl compounds such as hydrates, hydrogen sulphite addition compounds, acetals, imines and thioketones and enamines, since these also undergo the desired reaction with hydroxylamine or hydroxylamine O-methyl ether to give oximes or oxime O-methyl ethers. Likewise, geminal dihalo compounds as precursors of carbonyl compounds are part of the method according to the invention. In this case, halogen may be chlorine or bromine In the method according to the invention, organic carbonyl compounds of the formula (II) or quinones may be used which have a solubility in water of 0 to 30 g/l at 20° C. Preference is given to those compounds (II) or quinones which have a solubility in water of 0 to 20 g/l at 20° C., particularly preferably between 0 and 10 g/l, especially preferably between 0 and 3 g/l.

The compounds (II) or quinones used in accordance with the invention are therefore poorly soluble or insoluble in water. Preference is given to compounds of the formula (II) in which $R^3$ is $C_1$-$C_{12}$-alkyl, $C_3$-$C_{12}$-cycloalkyl, $C_2$-$C_{12}$-alkenyl, $C_6$-$C_{12}$-aryl, $C_1$-$C_6$-alkylaryl, 5-10-membered heterocycles and $C_1$-$C_4$-alkylhetaryl, wherein the alkyl residue, the cycloalkyl residue, the aryl residue, the alkylaryl residue, the heterocyclic residue or the alkylhetaryl residue may be substituted with one or more substituents selected from among F, Cl, Br, I, CN, $NO_2$, methyl, ethyl, propyl, butyl, $CF_3$, $CH_2F$, $CHF_2$, $CH_2CF_3$, $CH_2$—$CHF_2$, CHCl2, —OH, —OR, —OAr, carbonyl, COOR, =NOH, =N—OR, $CONH_2$, CONHR, CONRR', SR, RSO, $RSO_2$ and $R^4$ is hydrogen, $C_1$-$C_{12}$-alkyl, $C_3$-$C_{12}$-cycloalkyl, $C_6$-$C_{12}$-aryl, $C_1$-$C_6$-alkylaryl, COOR, $CONH_2$, CONHR, CONRR', wherein the alkyl residue, the cycloalkyl residue, the aryl residue, the alkylaryl residue, or the group R or R' may be substituted with one or more substituents selected from among F, Cl, Br, I, CN, $NO_2$, methyl, ethyl, propyl, butyl, $CF_3$, $CH_2F$, $CHF_2$, $CH_2CF_3$, $CH_2$—$CHF_2$, CHCl2, OH, OR, OAr, carbonyl, COOR, =N—OH, =N—OR, $CONH_2$, CONHR, CONRR', SR, RSO, $RSO_2$ and R and R' are mutually independently methyl, ethyl, propyl, butyl.

Particular preference is given to compounds of the formula (II) in which $R^3$ is pyridine, pyrazole, imidazole, triazole, furan, thiophene, pyrimidine, oxazole, thiazole, benzimidazole, indole, quinoline, wherein these may be substituted with one or more substituents selected from among F, Cl, Br, I, CN, $NO_2$, methyl, ethyl, propyl, butyl, $CF_3$, $CH_2F$, $CHF_2$, $CH_2CF_3$, $CH_2$—$CHF_2$, OH, OR, COOR, =N—OR, $CONH_2$, CONHR, CONRR', SR, RSO or $RSO_2$; $R^4$ is hydrogen, $C_1$-$C_{12}$-alkyl, $C_3$-$C_{12}$-cycloalkyl, phenyl, $C_1$-$C_6$-alkylphenyl, COOR, $CONH_2$, CONHR, CONRR', wherein the alkyl residue, the cycloalkyl residue, the phenyl residue, the phenylalkyl residue, or the group R or R' may be substituted with one or more substituents selected from among F, Cl, Br, I, CN, $NO_2$, methyl, ethyl, propyl, butyl, $CF_3$, $CH_2F$, $CHF_2$, $CH_2CF_3$, $CH_2$—$CHF_2$, OH, OR, COOR, =N—OR, $CONH_2$, CONHR, CONRR', SR, RSO, $RSO_2$ and R and R' are mutually independently methyl, ethyl, propyl, butyl.

Preference is likewise given to compounds of the formula (II) in which $R^3$ and $R^4$ together form an unsubstituted or substituted cycloalkyl residue having 3 to 10 carbon atoms, for example, cyclopentyl, cyclohexyl, 4-methylcyclohexyl, cycloheptyl, cyclooctyl or mono- or bicyclic terpenes, or a substituted or unsubstituted 5-10-membered heterocycle. Especially preferred are, for example, 4-methylacetophenone, 3-trifluoromethylacetophenone or 2,2-dichloro-4-methylacetophenone, α,α-dichloroacetophenone, 3,3-dimethyl-2-butanone, benzofuran-3-one, 4-t-butylcyclohexanone or DL-camphor, or benzoquinone.

Especially particular preference is given to compounds of the formula (II) such as 4-methylacetophenone, 3-trifluoromethylacetophenone, α,α-dichloroacetophenone, benzofuran-3-one, 3,3-dimethyl-2-butanone, or DL-camphor.

Suitable hydroxylamine salts or salts of hydroxylamine O-methyl ether of the formula (IV) according to the invention are the chlorides, sulphates or acetates thereof. Other salts formed by other mineral acids are also suitable and conceivable. Preference is given to using hydroxylammonium sulphate, hydroxylammonium chloride and O-methyl ethers thereof in accordance with the invention.

If a hydroxylamine salt or a salt of hydroxylamine O-methyl ether is used, the acid liberated by the reaction must be scavenged by addition of base (organic or inorganic base such as alkali metal hydroxides, carbonates, hydrogen carbonates, acetates, ammonia or amines). In accordance with the invention, preference is given to NaOH or KOH, sodium carbonate, potassium carbonate, sodium hydrogen carbonate, potassium hydrogen carbonate, sodium acetate and potassium acetate. The amount of base to be used may be varied, particularly when alkali metal and alkaline earth metal hydrogen carbonates or acetates are used as base. It has been found to be advantageous if the base is used in an amount of 0.5-1.2 equivalents, based on the salt of hydroxylamine or hydroxylamine O-methyl ether, particularly on the salt of hydroxylamine or hydroxylamine O-methyl ether of the formula (IV). The base may equally be used as the pure substance or as a solution, preferably an aqueous solution.

With the method according to the invention, oximes and oxime O-methyl ethers can be prepared in a very efficient, economic process from the carbonyl compounds on which they are based, particularly carbonyl compounds of the formula (II) or quinones.

The compounds of the formulae (Va) and (Vb) to be prepared according to the invention may optionally be present as mixtures of any different isomeric forms possible, especially of stereoisomers, for example E and Z isomers, threo and erythro isomers, and optical isomers, but if appropriate also of tautomers. Both the E and the Z isomers are included in the present application, as are the threo and erythro isomers, and also the optical isomers, any mixtures of these isomers, and also the possible tautomeric forms.

Compliance with the pH during the reaction according to the invention is important to ensure the activity of the compound of the formula (I). If a hydroxylamine salt or a salt of hydroxylamine O-methyl ether is used, the acid liberated by the reaction must be scavenged by addition of base. The latter is not applicable if a hydroxylammonium salt or salt of hydroxylamine O-methyl ether of a weak acid is used, i.e. a compound of the formula (IV) where $B^-$ is an anion of a weak base, e.g. acetate. The addition of the base can then be omitted.

The inorganic or organic bases which can be used in the reaction according to the invention are industrially readily available and inexpensive. Particularly suitable are alkali metal and alkaline earth metal hydroxides (e.g. NaOH, KOH), alkali metal and alkaline earth metal carbonates (e.g. sodium carbonate, potassium carbonate), alkali metal and alkaline earth metal hydrogen carbonates (e.g. sodium hydrogen carbonate, potassium hydrogen carbonate), alkali metal acetates (e.g. sodium acetate and potassium acetate), ammonia, or organic bases (e.g. triethylamine, pyridine). NaOH or KOH, sodium and potassium carbonates, hydrogen carbonates and acetates are preferred in accordance with the invention. Preference is given to using sodium hydroxide or potassium hydroxide as aqueous solutions.

The base is always added if the pH of the aqueous phase during the reaction is to be maintained in the desired range.

In the reaction according to the invention, the majority of the common solvents (e.g. aliphatic and cycloaliphatic hydrocarbons, aromatic hydrocarbons, chlorinated hydrocarbons, esters, alcohols, ethers and nitriles) may be used, whereby even in the industrial method, the inconvenient change of solvent can be omitted in the case that the subsequent reaction is to be conducted with another solvent. Critical in the selection of the solvent is that the solvent and water has an appropriately large miscibility gap in the reaction conditions used.

The reaction according to the invention takes place in an at least biphasic system composed of two liquid phases, namely an aqueous and an organic phase. The aqueous phase essentially comprises hydroxylamine or hydroxylamine O-methyl ether and/or salts thereof and optionally further salts as products of a neutralization reaction in the case that a base was present in the reaction.

The water phase as intended in the method is generated by using aqueous solutions of the compounds of the formula (III) or (IV) and/or by using the base in the form of aqueous solutions and/or by addition of water. In this case, a homogeneous aqueous solution does not necessarily need to be present in addition to the organic phase. Mixtures of two liquid and one solid phase are possible in the same manner and are part of the method according to the invention. Accordingly, the proportion of aqueous phase may be varied over a wide range. This proportion is generally guided by the industrial feasibility, such as the stirrability, of such mixtures.

The solvent optionally present in the reaction and/or the reactant, i.e. the carbonyl compound of the formula (II) or the quinone or the product (the compound of the formula (Va) or (Vb)) form the organic phase. If the compounds of the formula (Va), (Vb) and (II) themselves form a liquid organic phase under the reaction conditions, the addition of an organic solvent can be dispensed with.

Solvents in accordance with the invention are selected such that the carbonyl compounds and the products of the formula (Va) or (Vb) are readily soluble therein. Possible organic solvents are, for example, n-pentane, n-hexane, n-heptane, n-octane, n-nonane, n-decane, isohexane, isoheptane, isooctane, isodecane, isododecane, cyclopentane, cyclohexane, methylcyclohexane, tetralin, decalin, toluene, o-xylene, m-xylene, p-xylene, ethylbenzene, cumene, mesitylene, chlorobenzene, trifluoromethylbenzene, methylene chloride, 1,2-dichloroethane, methyl formate, ethyl formate, isopropyl formate, n-propyl formate, n-butyl formate, methyl acetate, ethyl acetate, n-propyl acetate, isopropyl acetate, n-butyl acetate, dimethyl carbonate, diethyl carbonate, ethylene carbonate, 1-butanol, 2-butanol, tert-butanol, pentanol, hexanol, 2-ethylhexanol, decanol, diisopropyl ether, t-butyl methyl ether (methyl t-butyl ether), di-n-butyl ether, methyl cyclopentyl ether, tetrahydrofuran, 1,2-dimethoxyethane, propionitrile, butyronitrile. Preferred solvents are methylcyclohexane, toluene, n-butyl acetate, t-butyl methyl ether (methyl t-butyl ether), petroleum ether, ligroin and benzine. The amount of solvents to be used may be varied in a very wide range and depends on the solubility of the carbonyl compound and the product of the formula (Va) or (Vb).

Preferred solvents are methylcyclohexane, toluene, n-butyl acetate, butanol or methyl tert-butyl ether.

Compounds of the formula (III) or (IV) are preferably added in aqueous solution.

The reaction temperature in the method according to the invention depends on the reactivity of the carbonyl compounds of the formula (II) or the quinone in the respective reaction mixtures. The reaction temperature can be in the range of 0° C. to 200° C., or 0° C. to 160° C. The reaction temperature is preferably in the range of 20° C. to 150° C., particularly preferably in the range of 40° C. to 120° C. The reaction takes place particularly at a reaction temperature in the range of 0° C. to 160° C.; the reaction temperature is preferably in the range of 30° C. to 120° C., very preferably in the range of 40° C. to 100° C.

If the method according to the invention is operated at temperatures above 105° C., a pressurised procedure results which is part of the method according to the invention in a particular embodiment.

The amount of the compound of the formula (III) and (IV) used is advantageously maintained close to the stoichiometric requirements, although slight excesses, e.g. up to 20 mol %, may be advantageous for a complete conversion. The use of greater excesses is possible without disadvantages, although this is not economic.

The compounds of the formula (IV) may be used in a similar manner as solids or as aqueous solutions. When using aqueous solutions, these can be varied over a wide concentration range of 2 to 70% by weight, preferably 5-50% by weight, particularly preferably 10-50% by weight.

In one configuration [A] of the method according to the invention, the carbonyl compound of the formula (II) or the quinone, together with the compound of the formula (III) or (IV), the solvent, the water, the phosphoric ester of the formula (I) and optionally the base are charged and brought to the reaction temperature. Such a procedure is possible both in a continuous and in a batchwise process variant.

In one configuration [B] of the method according to the invention, the carbonyl compound of the formula (II) or the quinone with the solvent, the water and the phosphoric ester of the formula (I) are charged and the compound of the formula (III) or (IV) and optionally the base are added under the desired reaction conditions.

In one configuration [C] of the method according to the invention, the compound of the formula (III) or (IV) with the solvent, the water and the phosphoric ester of the formula (I) are charged and the compound of the formula (II) or the quinone and optionally the base are added under reaction conditions.

In one configuration [D] of the method according to the invention, the compound of the formula (III) and/or (IV) with the solvent, the water, the phosphoric ester of the formula (I) and optionally the base are charged and the compound of the formula (II) or the quinone is added.

Which of the configurations [A] to [D] is used depends on factors such as substance properties and the operational safety of the method. The preferred method configurations are those which ensure a consistent removal of the heat of reaction in the operating method, which is possible by charging of one reaction component and addition of the other or by a parallel addition of all reaction components.

The method according to the invention is described in the examples which follow, but the method is not intended to be limited to the examples.

The reaction mixtures in the examples were analyzed by means of HPLC or GC by area %.

| HPLC method: | Column | Kinetex 2.6 u C18 100A |
| --- | --- | --- |
| | Temperature | 50° C. |
| | Eluent | Water/0.1% H3PO4 (90%), CH3CN (10%) |
| | Wavelength | 220 nm |
| GC method: | Column | DB1/DB-1701 |
| | Length, ID, Film | 10 m, 0.1 mm, 0.1 μm |
| | Injector | Split/Split ratio 1:50 |
| | | Constant flow; flow rate 0.45 ml/min. |
| | | Temp. 250° C., injection volume 0.2 μl |
| | Mobile Phase | Hydrogen |
| | Detector | FID - Temp. 320° C. |
| | Oven Temperature Program | 50° C. to 320° C. (30 K/min.) |

EXAMPLES

Example 1

50 g of methylcyclohexane, 75.1 g of a 40% aqueous solution of hydroxylammonium sulphate (0.183 mol based on the molecular weight 164.14) and 0.6 g (0.002 mol) of di(2-ethylhexyl)phosphoric acid (95%) were charged in a 250 ml glass reactor equipped with heating jacket, stirrer and reflux condenser and the mixture was heated to 70° C. At this temperature under vigorous stirring, 47 g (0.33 mol) of 4-methylacetophenone (95%) over a period of 30 minutes, and subsequently 43.7 g (0.35 mol) of aqueous sodium hydroxide solution (32%) over a period of 20 minutes, were uniformly added using metering pumps. The pH after completion of the addition of the aqueous sodium hydroxide solution was 6.5. The reaction mixture was further stirred at 70° C. for 60 minutes. The stirrer was then stopped and the organic phase was separated and analyzed by HPLC (Column: Kinetex 2.6 u C18 100A, 50° C., H2O/CH3CN, 220 nm).

Result: 4-Methylacetophenone: 0.2% (HPLC peak area)
4-Methylacetophenone oxime, sum of E and Z isomers: 98.8% (HPLC peak area)
The proportion of reactant and product in the aqueous phase is negligible.

Example 2

Comparative Example

Performed as in Example 1 but with the difference that it was carried out without addition of di(2-ethylhexyl)phosphoric acid.

Result: 4-Methylacetophenone: 56.6% (HPLC peak area)
4-Methylacetophenone oxime, sum of E and Z isomers: 42.1% (HPLC peak area)

Example 3

Performed as in Example 1 with the difference that 3-trifluoromethylacetophenone was used.

Result with di(2-ethylhexyl)phosphoric acid:
3-Trifluoromethylacetophenone: 0.2% (HPLC peak area)
3-Trifluoromethylacetophenone oxime: 99.8% (HPLC peak area)

Example 4

Comparative Example

Performed as in Example 2 with the difference that 3-trifluoromethylacetophenone was used.

Result without di(2-ethylhexyl)phosphoric acid:
3-Trifluoromethylacetophenone: 68.7% (HPLC peak area)
3-Trifluoromethylacetophenone oxime: 31.3% (HPLC peak area)

Example 5

Performed as in Example 1 with the difference that 3,3-dimethyl-2-butanone was used and the determination of the conversion was carried out by GC.

Result with di(2-ethylhexyl)phosphoric acid:
3,3-Dimethyl-2-butanone: <0.05% (GC, peak area)
3,3-Dimethyl-2-butanone oxime: 100% (GC, peak area)

Example 6

Comparative Example

Performed as in Example 2 with the difference that 3,3-dimethyl-2-butanone was used and the determination of the conversion was carried out by GC.
Result without di(2-ethylhexyl)phosphoric acid:
3,3-Dimethyl-2-butanone: 36.8% (GC, peak area)
3,3-Dimethyl-2-butanone oxime: 63.2% (GC, peak area)

Example 7

Performed as in Example 1 with the difference that DL-camphor was used and the temperature in the addition step and the stirring period was maintained at 85° C. The conversion was determined by GC.
Result with di(2-ethylhexyl)phosphoric acid:
DL-Camphor: 12.6% (GC, peak area)
DL-Camphor oxime: 87.4% (GC, peak area)

Example 8

Comparative Example

Performed as in Example 2 with the difference that DL-camphor was used and the temperature in the addition step and the stirring period was maintained at 85° C. The conversion was determined by GC.
Result without di(2-ethylhexyl)phosphoric acid:
DL-Camphor: 99.4% (GC, peak area)
DL-Camphor oxime: 0.6% (GC, peak area)

Examples 9-12

Various Catalysts, Table 1

50 g of methylcyclohexane, 75.1 g of a 40% aqueous solution of hydroxylammonium sulphate (0.183 mol based on the molecular weight 164.14) and (0.002 mol) of the catalysts listed in Table 1 were charged in a 250 ml glass reactor equipped with heating jacket, stirrer and reflux condenser and the mixture was heated to 70° C. Subsequently, at this temperature and under vigorous stirring, 47 g (0.33 mol) of 3-trifluoromethylacetophenone (95%) over a period of 30 minutes, and 43.7 g (0.35 mol) of aqueous sodium hydroxide solution (32%) over a period of 20 minutes, were consecutively uniformly added using metering pumps. The reaction mixture was further stirred at 70° C. for 60 minutes. The stirrer was then stopped and the organic phase was separated and analyzed by HPLC.

TABLE 1 relating to examples 9-12:

| Example | Catalyst | 3-Trifluoro-methylaceto-phenone % (HPLC, peak area) | 3-Trifluoro-methylaceto-phenone oxime % (HPLC, peak area) |
| --- | --- | --- | --- |
| 9 | Di-n-butyl hydrogen phosphate | 0.2 | 99.8 |
| 10 | Mono-n-butyl dihydrogen phosphate | 3.0 | 97.0 |
| 11 | Monooleyl dihydrogen phosphate | 3.6 | 96.4 |
| 12 | Bis(dodecyloxy)phosphorylamine | 3.4 | 96.6 |

Examples 13-16

Solvent, Table 2

65 ml of solvent, 75.1 g of a 40% aqueous solution of hydroxylammonium sulphate (0.183 mol based on the molecular weight 164.14) and 0.6 g (0.002 mol) of di(2-ethylhexyl)phosphoric acid were charged in a 250 ml glass reactor equipped with heating jacket, stirrer and reflux condenser and the mixture was heated to 70° C. (using methyl t-butyl ether as solvent, to 50° C.). Subsequently, at this temperature and under vigorous stirring, 64 g (0.33 mol) of 3-trifluoromethylacetophenone (98%) over a period of 60 minutes, and 43.7 g (0.35 mol) of aqueous sodium hydroxide solution (32%) over a period of 20 minutes, were consecutively uniformly added using metering pumps. The reaction mixture was further stirred for 60 minutes at 70° C. (using methyl t-butyl ether as solvent, to 50° C.). The stirrer was then stopped and the organic phase was separated and analyzed by HPLC. The results are summarized in the Table for examples 13-20.

TABLE 2 relating to examples 13-20:

| Example | Solvent | 3-Trifluoromethyl-acetophenone | 3-Trifluoromethyl-acetophenone oxime |
| --- | --- | --- | --- |
| 13 | Toluene | n.d. | 99.2 |
| 14 (comparative example without cat.) | Toluene | 91.7 | 7.4 |
| 15 | n-Butyl acetate | 0.3 | 98.1 |
| 16 (comparative example without cat.) | n-Butyl acetate | 89.4 | 8.5 |
| 17 | Butanol | 3.1 | 96.3 |
| 18 (comparative example without cat.) | Butanol | 28.1 | 71.2 |
| 19 | Methyl t-butyl ether | 1.2 | 98.2 |
| 20 (comparative example without cat.) | Methyl t-butyl ether | 95.4 | 3.8 |

Example 21

50 g of toluene, 75.1 g of a 40% aqueous solution of hydroxylammonium sulphate (0.183 mol based on the molecular weight 164.14) and 0.6 g (0.002 mol) of di(2-ethylhexyl)phosphoric acid (95%) were charged in a 500 ml glass reactor equipped with heating jacket, stirrer and reflux condenser and the mixture was heated to 40° C. At this temperature under vigorous stirring, a solution of 45.6 g (0.33 mol) of benzofuran-3-one (97%) in 100 g of toluene over a period of 30 minutes, and subsequently 43.7 g (0.33 mol) of aqueous sodium hydroxide solution (32%) over a period of 20 minutes, were uniformly added using metering pumps. The pH after completion of the addition of the aqueous sodium hydroxide solution was 5.5. The reaction mixture was further stirred at 40° C. for 60 minutes. A sample was removed from the stirred mixture and analyzed by HPLC (column: Kinetex 2.6 u C18 100A, 50° C., $H_2O/CH_3CN$, 220 nm).

Result: Benzofuran-3-one: 0.2% (HPLC peak area)
Benzofuran-3-one oxime, sum of E and Z isomers: 97.5% (HPLC peak area)

Example 22

Comparative Example

Performed as in Example 21 but with the difference that it was carried out without addition of di(2-ethylhexyl) phosphoric acid.
Result: Benzofuran-3-one: 42.5% (HPLC peak area)
Benzofuran-3-one oxime, sum of E and Z isomers: 54.3% (HPLC peak area)

Example 23

30 g of methylcyclohexane, 46.0 g of a 25% aqueous solution of hydroxylamine O-methyl ether hydrochloride and 0.4 g (0.001 mol) of di(2-ethylhexyl)phosphoric acid (95%) were charged in a 250 ml glass reactor equipped with heating jacket, stirrer and reflux condenser and the mixture was heated to 70° C. Subsequently, at this temperature and under vigorous stirring, 25 g (0.13 mol) of 3-trifluoromethylacetophenone (98%) over a period of 60 minutes, and 16 g (0.13 mol) of aqueous sodium hydroxide solution (32%) over a period of 20 minutes, were consecutively uniformly added using metering pumps. The reaction mixture was further stirred at 70° C. for 60 minutes. The stirrer was then stopped and the organic phase was separated and analyzed by HPLC.
Result: 3-Trifluoromethylacetophenone: <0.1% (HPLC peak area)
4-Trifluoromethylacetophenone oxime O-methyl ether, sum of E and Z isomers: 99.5% (HPLC peak area)

Example 24

Comparative Example to Example 23

Performed as in Example 21 but with the difference that it was carried out without addition of di(2-ethylhexyl) phosphoric acid.
Result: 3-Trifluoromethylacetophenone: 32.2% (HPLC peak area)
4-Trifluoromethylacetophenone oxime O-methyl ether, sum of E and Z isomers: 68.2% (HPLC peak area)

Example 25

In sequence, 70 g of a 40% aqueous solution of hydroxylammonium sulphate (0.17 mol based on the molecular weight 164.14), 28.1 g (0.34 mol) of sodium acetate (99%), 0.3 g (0.001 mol) of di(2-ethylhexyl)phosphoric acid (95%) and 30.8 g of methylcyclohexane were charged in a 250 ml glass reactor equipped with heating jacket, stirrer and reflux condenser. The mixture was heated to 70° C. and adjusted to a pH of 6 with 35.0 g of aqueous sodium hydroxide solution (30%). Subsequently, 30 g (0.15 mol) of α,α'-dichloromethylacetophenone (97%) were added over 30 minutes at 70° C. After stirring for 3 h, a representative sample was removed from the reaction suspension and analyzed by HPLC (column: Kinetex 2.6 u C18 100A, 50° C., $H_2O$/$CH_3CN$, 220 nm).

Result: α,α'-Dichloromethylacetophenone: 4.2% (HPLC peak area)
Phenylglyoxal dioxime, sum of isomers: 93.8% (HPLC peak area)

Example 26

Comparative Example to Example 25

Performed as in Example 25 but with the difference that it was carried out without addition of di(2-ethylhexyl) phosphoric acid.
Result: α,α'-Dichloromethylacetophenone: 72.5% (HPLC peak area)
Phenylglyoxal dioxime, sum of isomers: 24.7% (HPLC peak area)

The invention claimed is:
1. Method for preparing an oxime of formula (Va) or an oxime O-methyl ether of formula (Vb)

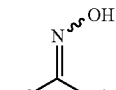

(Va)

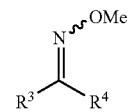

(Vb)

in which
$R^3$ is $C_1$-$C_{12}$-alkyl, $C_3$-$C_{12}$-cycloalkyl, $C_2$-$C_{20}$-alkenyl, $C_6$-$C_{14}$-aryl, $C_1$-$C_6$-alkylaryl, 5-10-membered heterocycles and $C_1$-$C_6$-alkylhetaryl, wherein the alkyl residue, the cycloalkyl residue, the alkenyl residue, the aryl residue, the alkylaryl residue or the heterocyclic residue or the alkylhetaryl residue may be substituted with one or more substituents selected from among halogen, CN, $NO_2$, $C_1$-$C_6$-alkyl, $C_1$-$C_6$-haloalkyl, —OH, —OR, —COOR, =N—OR, $CONH_2$, CONHR, CONRR', SR, RSO, $RSO_2$, —OAr, carbonyl, =NOH;
$R^4$ is hydrogen, $C_1$-$C_{18}$-alkyl, $C_3$-$C_{12}$-cycloalkyl, $C_6$-$C_{14}$-aryl, $C_1$-$C_6$-alkylaryl, COOR, $CONH_2$, CONHR, CONRR', wherein the alkyl residue, the cycloalkyl residue, the aryl residue, the alkylaryl residue or the group R or R' may be substituted with one or more substituents selected from among halogen, CN, $NO_2$, $C_1$-$C_6$-alkyl, $C_1$-$C_6$-haloalkyl, OH, OR, COOR, C=N—OR, $CONH_2$, CONHR, CONRR', SR, RSO, $RSO_2$, OAr, carbonyl, =N—OH and
R and R' are mutually independently unsubstituted or substituted $C_1$-$C_6$-alkyl; or
$R^3$ and $R^4$ together form an unsubstituted or substituted cycloalkyl residue having 3 to 10 carbon atoms, or a substituted or unsubstituted 5-10-membered heterocycle;
Comprising reacting a quinone, or a carbonyl compound of the formula (II)

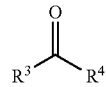

(II)

in which the residues $R^3$ and $R^4$ have the meanings mentioned above and the compounds (II) have a solubility in water of 0 to 30 g/l, optionally 0 to 20 g/l at 20° C.,
with the free base of hydroxylamine of the formula (III) or with a salt of hydroxylamine or hydroxylamine O-methyl ether of the formula (IV)

(III)
(IV)

in which
$R^5$ is hydrogen,
$R'^5$ is hydrogen or methyl,
$B^-$ is an anion, which is selected from among chloride, sulphate, phosphate, hydrogen phosphate, dihydrogen phosphate, carbonate, hydrogen carbonate and acetate, and
in the presence of a phosphoric ester of formula (I) and/or a salt thereof,

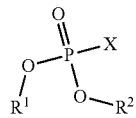
(I)

in which
X is OH and
$R^1$ and $R^2$ are mutually independently hydrogen, $C_1$-$C_{18}$-alkyl, $C_2$-$C_{20}$-alkenyl, $C_3$-$C_{12}$-cycloalkyl, phenyl or $C_1$-$C_6$-alkylphenyl, wherein the alkyl residue, the alkenyl residue or the cycloalkyl residue may be substituted in each case with one or more substituents selected from among halogen, CN and $NO_2$ and wherein the phenyl residue may in addition be mono- or polysubstituted with $C_1$-$C_6$-alkyl and/or $C_1$-$C_6$-haloalkyl;

in an at least biphasic mixture consisting of an aqueous and organic phase wherein the pH (at RT) in the aqueous phase during the reaction is in a range of 2 to 10.

2. Method according to claim 1, wherein the phosphoric ester of the formula (I) is di(2-ethylhexyl)phosphoric acid, di-n-butylphosphoric acid, mono-n-butylphosphoric acid or monooleylphosphoric acid.

3. Method according to claim 1, wherein the reaction takes place in the presence of an organic or inorganic base selected from among alkali metal and alkaline earth metal hydroxides, alkali metal and alkaline earth metal carbonates, alkali metal and alkaline earth metal hydrogen carbonates, alkali metal acetates, ammonia or organic bases.

4. A method for preparing an oxime of formula (Va) according to claim 1, wherein $R^3$ is phenyl and $R^4$ is methyl.

* * * * *